United States Patent
Serban et al.

(10) Patent No.: US 10,429,333 B2
(45) Date of Patent: Oct. 1, 2019

(54) RELATIVE HUMIDITY SENSOR AND METHOD

(71) Applicant: HONEYWELL INTERNATIONAL INC., Morris Plains, NJ (US)

(72) Inventors: Bogdan-Catalin Serban, Bucharest (RO); Cornel P. Cobianu, Bucharest (RO); Mihai Brezeanu, Bucharest (RO); Octavian Buiu, Bucharest (RO); Cazimir Gabriel Bostan, Bucharest (RO); Alisa Stratulat, Bucharest (RO)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 464 days.

(21) Appl. No.: 15/090,075

(22) Filed: Apr. 4, 2016

(65) Prior Publication Data

US 2016/0299095 A1    Oct. 13, 2016

(30) Foreign Application Priority Data

Apr. 9, 2015   (EP) .................................... 15163039

(51) Int. Cl.
  *G01N 27/22*          (2006.01)
(52) U.S. Cl.
  CPC ......... *G01N 27/223* (2013.01); *G01N 27/225* (2013.01)
(58) Field of Classification Search
  CPC ........................... G01N 27/223; G01N 27/225
  See application file for complete search history.

(56) References Cited

U.S. PATENT DOCUMENTS

| | | | | |
|---|---|---|---|---|
| 4,522,060 A * | 6/1985 | Murata | ................ | G01N 27/223 324/696 |
| 4,547,310 A * | 10/1985 | Kasanami | .......... | H01C 17/0658 106/311 |
| 4,621,249 A * | 11/1986 | Uchikawa | ........ | H01C 17/06586 338/34 |
| 4,860,584 A * | 8/1989 | Mercer | ................ | G01N 27/121 73/335.03 |
| 4,876,890 A * | 10/1989 | Mercer | ................ | G01N 27/225 73/335.03 |
| 4,920,451 A * | 4/1990 | Sakai | ................... | G01N 27/225 361/286 |

(Continued)

FOREIGN PATENT DOCUMENTS

| | | | | |
|---|---|---|---|---|
| EP | 2294137 B1 * | 4/2015 | ............. | C08L 77/02 |
| WO | WO 0175429 A1 * | 10/2001 | ........... | G01N 27/121 |

(Continued)

OTHER PUBLICATIONS

Machine translation of EP 2294137 B1.*

(Continued)

*Primary Examiner* — David J Bolduc
(74) *Attorney, Agent, or Firm* — Alston & Bird LLP (57) ABSTRACT

A relative humidity sensor is disclosed. The relative humidity sensor includes a first electrode and a second electrode disposed above a dielectric substrate. A sensitive layer is disposed above at least one of the first electrode and the second electrode, where the sensitive layer is formed from a composition including a polyimide and a hydrophobic filler. A dust protection layer is disposed above the sensitive layer.

20 Claims, 4 Drawing Sheets

(56) References Cited

U.S. PATENT DOCUMENTS

| | | | | |
|---|---|---|---|---|
| 4,965,698 | A | * 10/1990 | Thoma | G01M 3/16 29/25.42 |
| 5,050,434 | A | 9/1991 | Demisch | |
| 5,069,069 | A | 12/1991 | Miyagishi et al. | |
| 5,161,085 | A | 11/1992 | Sakai et al. | |
| 5,177,662 | A | * 1/1993 | Thoma | G01N 27/225 29/25.42 |
| 5,348,761 | A | * 9/1994 | Mitter | G01M 3/045 252/408.1 |
| 5,408,381 | A | 4/1995 | Thoma et al. | |
| 5,833,877 | A | * 11/1998 | Elliott | B01D 21/01 252/299.01 |
| 6,114,863 | A | * 9/2000 | Krahn | G01N 27/02 324/664 |
| 6,323,659 | B1 | * 11/2001 | Krahn | G01N 27/223 324/554 |
| 7,016,463 | B2 | * 3/2006 | Moriyama | G01N 23/223 378/45 |
| 2003/0179805 | A1 | * 9/2003 | Hamamoto | G01N 27/225 374/16 |
| 2004/0008471 | A1 | * 1/2004 | Davis | G01D 5/24 361/306.3 |
| 2004/0080325 | A1 | * 4/2004 | Ogura | G01N 27/225 324/664 |
| 2004/0177685 | A1 | * 9/2004 | Yokura | G01N 27/225 73/335.04 |
| 2004/0182153 | A1 | * 9/2004 | Hamamoto | G01N 27/225 73/335.04 |
| 2004/0194546 | A1 | * 10/2004 | Kanehori | G01N 27/225 73/335.04 |
| 2004/0244482 | A1 | * 12/2004 | Schultz | G01N 27/225 73/335.01 |
| 2004/0254306 | A1 | * 12/2004 | Isogai | G01N 27/121 525/435 |
| 2007/0210807 | A1 | * 9/2007 | Arisaka | G01N 27/225 324/664 |
| 2007/0290379 | A1 | * 12/2007 | Dueber | C08G 73/1039 257/792 |
| 2008/0118633 | A1 | * 5/2008 | Chen | H01C 17/06586 427/101 |
| 2008/0185561 | A1 | * 8/2008 | Summers | C08G 59/245 252/511 |
| 2009/0056439 | A1 | * 3/2009 | Suzuki | G01N 27/223 73/335.02 |
| 2009/0134026 | A1 | * 5/2009 | Langenbacher | G01N 27/225 204/424 |
| 2009/0141767 | A1 | * 6/2009 | Cummins | G01N 27/223 374/142 |
| 2010/0134948 | A1 | * 6/2010 | Park | G01N 27/223 361/286 |
| 2010/0307238 | A1 | * 12/2010 | Van Popta | G01N 27/225 73/335.04 |
| 2011/0217573 | A1 | * 9/2011 | Kritzer | G01F 23/263 429/61 |
| 2011/0226041 | A1 | * 9/2011 | Cummins | G01N 27/223 73/25.01 |
| 2011/0239759 | A1 | * 10/2011 | Cobianu | G01N 29/022 73/335.03 |
| 2011/0297891 | A1 | * 12/2011 | Mercx | C08L 23/04 252/511 |
| 2012/0000285 | A1 | * 1/2012 | Waga | G01N 27/225 73/335.04 |
| 2012/0071362 | A1 | * 3/2012 | Nhan | G01N 33/0047 506/33 |
| 2012/0260732 | A1 | * 10/2012 | Humbert | G01N 27/223 73/335.05 |
| 2012/0304742 | A1 | * 12/2012 | Cummins | G01N 27/121 73/31.06 |
| 2013/0063163 | A1 | * 3/2013 | Sim | G01N 27/223 324/663 |
| 2013/0088244 | A1 | * 4/2013 | Gryska | G01N 27/226 324/658 |
| 2013/0336842 | A1 | * 12/2013 | Grange | G01N 27/223 422/90 |
| 2014/0009174 | A1 | * 1/2014 | Youssi | G01N 27/223 324/665 |
| 2014/0076048 | A1 | * 3/2014 | Gryska | G01N 27/223 73/335.04 |
| 2015/0153296 | A1 | * 6/2015 | Gryska | G01N 27/121 73/335.04 |
| 2015/0168330 | A1 | * 6/2015 | Gryska | G01N 27/223 324/663 |
| 2015/0185175 | A1 | * 7/2015 | Palazzotto | G01N 27/223 324/663 |
| 2016/0236803 | A1 | * 8/2016 | Torii | B65B 1/22 |

FOREIGN PATENT DOCUMENTS

| | | | |
|---|---|---|---|
| WO | WO-2007/146382 A2 | 12/2007 | |
| WO | WO-2009/153204 A1 | 12/2009 | |
| WO | WO 2009153204 A1 | * 12/2009 | ............. C08L 77/02 |

OTHER PUBLICATIONS

Serban et al, Talc-Impregnated Polyimide for Humidity Sensors with Improved Hysteresis, 2015 International Semiconductor Conference (CAS); 2015, p. 109-112.*

"European Application Serial No. 15163039.9, Extended European Search Report dated Oct. 8, 2015", 5 pgs.

"Lignin Applications: Brief Overview", [online]. Retrieved from the Internet: <URL: http://www.ipst.gatech.edu/faculty/ragauskas_art/technical_reviews/Lignin%20Applications2.pdf, (Jan. 2013), 17 pgs.

Beerlage, Monique A. M., "Polyimide ultrafiltration membranes for non-aqueous systems", PhD Thesis, Universiteit Twente, (1994), 228 pgs.

Chen, Zhi, et al., "Humidity Sensors: A Review of Materials and Mechanisms", *Sensor Letters*, vol. 4, (2005), 274-295.

Kwon, Jinuk Kwon,, et al., "Water sorption behavior in polyimide thin films controlled by inorganic additives", *Macromolecular Research*, 22(4), (Apr. 2014), 431-435.

Picot, M., et al., "A versatile route to modify polyethersulfone membranes by chemical reduction of aryldiazonium salts", *Journal of Membrane Science*, vols. 417-418, (2012), 131-136.

Ralston, Andrew R. K., et al., "A model for the relative environmental stability of a series of polyimide capacitance humidity sensors", *Sensors and Actuators B*, 34, Issues 1-3, (1994), 343-348.

Yudin, V E, et al., "New polyimide nanocornposites based on silicate type nanotubes: Dispersion, processing and properties", *Polymer*, vol. 48, No. 5,, (2007), 1306-1315.

\* cited by examiner

RELATIVE HUMIDITY SENSOR AND METHOD

RELATED APPLICATIONS

This application claims the benefit of priority under 35 U.S.C. Section 119 to European Patent Application Serial No. 15163039.9, filed on Apr. 9, 2015, which application is incorporated herein by reference in its entirety.

BACKGROUND

Relative humidity sensors can be used in various domestic and industrial environments. For example, relative humidity sensors can be used for control of the living environment in buildings, textiles and paper manufacturing, food processing, the medical field, the automotive industry, pharmaceutical processing, agriculture, and chemical gas purification, among others.

SUMMARY

A relative humidity sensor is disclosed. The relative humidity sensor includes a first electrode and a second electrode disposed above a dielectric substrate, a sensitive layer disposed above at least one of the first electrode and the second electrode, the sensitive layer is formed from a composition including a polyimide and a hydrophobic filler, and a dust protection layer disposed above the sensitive layer.

In an example, a method of forming a relative humidity sensor includes depositing a first electrode on a dielectric substrate, applying a composition to an upper surface of the first electrode to form a sensitive layer, the composition including a polyimide and a hydrophobic filler, depositing a second electrode on an upper surface of the sensitive layer, and depositing a dust protection layer on an upper surface of the second electrode.

In an example, a method of forming a relative humidity sensor includes preparing a composition, the composition including a polyimide and a hydrophobic filler, and depositing at least a portion of the composition on a dielectric substrate supporting a first electrode and a second electrode, wherein the first and second electrode are interdigitated, to form the relative humidity sensor.

DETAILED DESCRIPTION OF THE DRAWINGS

The embodiments of the present disclosure will be described, by way of example only, by reference to the FIGS. 1-5 of the accompanying drawing in which.

DETAILED DESCRIPTION

The present disclosure is directed toward a relative humidity sensor and a method for making the relative humidity sensor. The relative humidity sensor can incorporate a sensitive layer formed from a composition including a polyimide and a hydrophobic filler. The hydrophobic filler can, in an example, be an organic compound, such as a lignin. In an example, the hydrophobic filler can be an inorganic compound, such as talc. The relative humidity sensor can, in an example, be formed in stacked configuration or in an interdigitated configuration.

Capacitive sensors are commonly used at least due in part to their linear response. That is, the amount of water absorbed, which is proportional to the relative humidity of the environment, is linearly proportional to the change of the dielectric constant of the insulating polymer of the capacitive sensor. Previous and current capacitive sensors can suffer from hysteresis. Previous approaches have attempted to mitigate the hysteresis problem by incorporation of hydrophobic carbon black within the polymer. However, carbon black is not fully compatible with polymer matrices. The present disclosure provides a relative humidity sensor including a sensitive layer formed of polyimide and a polyimide compatible hydrophobic filler, so as to mitigate or prevent the hysteresis.

Figure 1:
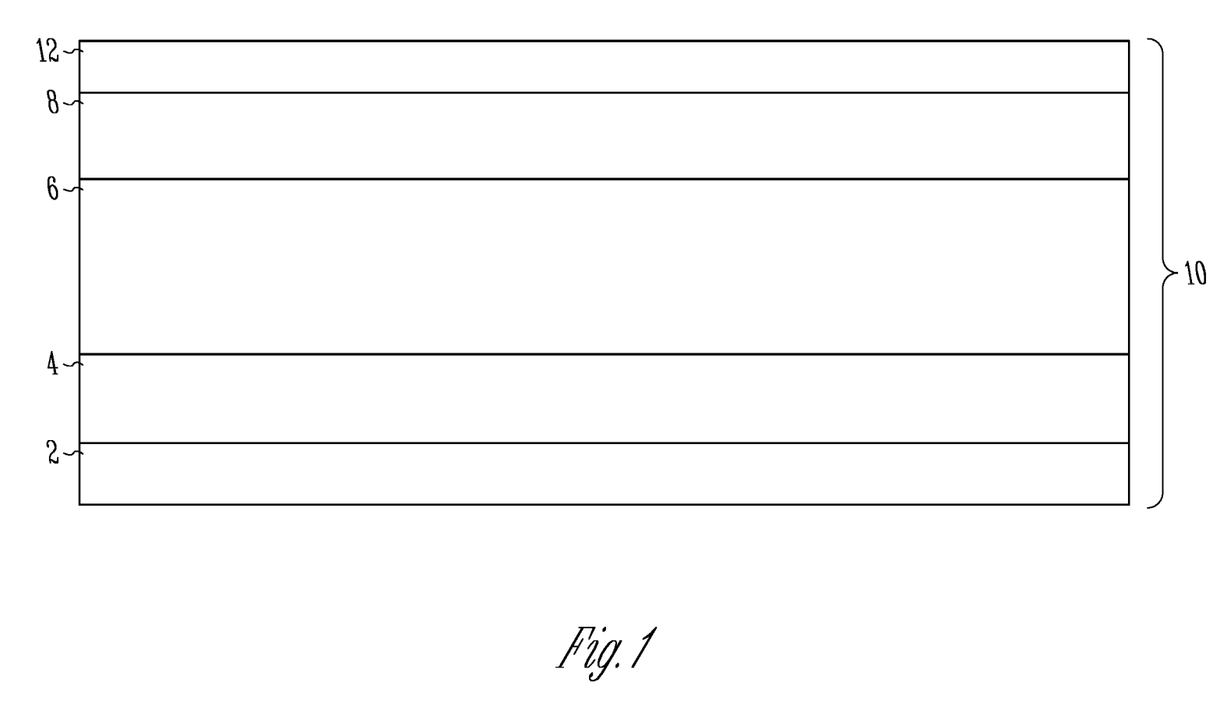
FIG. 1 shows a cross-sectional view of a relative humidity sensor, in accordance with at least on example.

FIG. 1 shows a cross-sectional view of a relative humidity sensor 10 (hereinafter "sensor 10"), in accordance with at least one example. The sensor 10 illustrated in FIG. 1 is a stacked configuration, but examples are not so limited (e.g., FIGS. 2 and 3). The sensor 10 can include a dielectric substrate 2. In an example, the dielectric substrate 2 can be formed of a flexible dielectric material such that the dielectric substrate 2 can conform to non-planar surfaces. In another example, the dielectric substrate 22 is not flexible. The dielectric substrate 2 can include a polymer, such as a polyimide. The dielectric substrate 2, in an example, can be formed from commercially available Kapton® (with thickness from 50 to 125 µm). The sensor 10 can include a first electrode 4 and a second electrode 8. In an example, the first electrode 4 and the second electrode 8 can have the same composition or can be formed of different compositions. In an example, the first electrode 4, the second electrode 8, or both is formed from a conductive polymer, such as a polymer including conductive carbon (e.g., carbon black), with thickness from 1 to 2 µm for layers obtained by direct printing. In an example, the first electrode 4, the second electrode 8, or both are formed from conductive Kapton®. The first electrode 4, the second electrode 4, or both can be a conductive material such as metal, a conductive polymer, or the like.

As shown in FIG. 1, the sensor 10 can include a sensitive layer 6, of thickness from 1 to 2 µm for layers obtained by direct printing. The sensitive layer 6 can be formed from a composition including a polyimide and a hydrophobic filler. The polyimide can, in an example, include one or more polymer having imide monomers. For example, the polyimide can include at least one commercially available product, such as, but not limited to, P84® (described by formula (1)), Matrimid® 5218 (described by formula (2)), Kapton® (described by formula (3)), and Upilex® R (described by formula (4)).

As discussed herein, the composition can be prepared by mixing the polyimide with the hydrophobic filler or can be prepared by synthesizing a functionalized polyimide, preparing a solution of the functionalized polyimide, and mixing the functionalized polyimide solution with the hydrophobic filler.

In an example, the hydrophobic filler can include an organic compound. The organic compound can, in an example, include one or more lignin with different molecular weight. A benefit of including lignin in the composition can include reducing water up-take of the sensitive layer 6 formed from the composition. In an example, the lignin can have an average molecular weight between about 400 g/mol, about 500 g/mol, about 600 g/mol, about 700 g/mol, about 800 g/mol, about 900 g/mol, about 1000 g/mol, or about 1100 g/mol or greater. In an example, the lignin can have an average molecular weight of about 500 g/mol to about 1000 g/mol. The composition can include about 0.5% weight lignin based on a total weight of the composition (wt/wt %), 1.0 wt/wt %, 2.0 wt/wt %, 3 wt/wt %, 4 wt/wt %, 5 wt/wt %, 6 wt/wt %, 7 wt/wt %, 8 wt/wt %, 9 wt/wt %, 10 wt/wt %, or about 11 wt/wt % or greater. In an example, the lignin can be about 1 wt/wt % to about 10 wt/wt %.

In an example, the hydrophobic filler can include an inorganic compound. The inorganic compound can, in an example include talc nanoparticles. As described herein, a nanoparticles includes any particles with a dimension in the range of about 1 nanometer (nm) to about 100 nm. A benefit of including talc nanoparticles in the composition can include increasing the hydrophobicity of the polyimide used in forming the sensitive layer 6. In an example, the talc particles can include hydrated magnesium covered silica represented by the chemical formula $Mg_3Si_4O_{10}(OH)_2$. The composition can include about 0.25% weight talc nanoparticles based on a total weight of the composition (wt/wt %), 0.5 wt/wt %, 1.5 wt/wt %, 1.5 wt/wt %, 2.0 wt/wt %, 2.5 wt/wt %, 3.5 wt/wt %, 4.0 wt/wt %, 4.5 wt/wt %, 5.0 wt/wt %, 5.5 wt/wt %, 6.0 wt/wt %, 6.5 wt/wt %, or about 7.0 wt/wt % or greater. In an example, the talc nanoparticles can be about 1 wt/wt % to about 5 wt/wt %.

As shown in FIG. 1, the sensor 10 can include a dust protection layer 12 disposed above the sensitive layer 6, with thickness of 1 to 2 μm. In an example, the dust protection layer 12 is formed from a polymer, such as a polyimide, as described herein. The dust protection layer 12 should be a barrier against dust and in the same time it should be enough porous to allow air and humidity to reach the sensing layer without affecting the response time of the sensor. This dust protection layer can be formed from the same or different material as the dielectric substrate 2. In an example, due its higher porosity with respect to sensing layer, the dust protection layer 12 can be less hydrophobic than sensitive layer 6. The dust protection layer 12 can, in an example, be formed from commercially available higher porosity Kapton®.

As discussed herein, FIG. 1 illustrates the sensor 10 in a stacked configuration. A stacked configuration can include the second electrode 8 disposed above the first electrode 4. As shown, the first electrode 4 and the second electrode 8 are separated by the sensitive layer 6. The sensitive layer 6 can be in electrical contact with the first electrode 4 and the second electrode 8. That is, the sensor 10 can include a stacked configuration, from bottom to top, including the dielectric substrate 2, the first electrode 4, the sensitive layer 6, the second electrode 8, and the dust protective layer 12. Although the sensor 10 is shown as having a rectangular cross-sectional geometry, examples are not so limited. In an example, the sensor 10 can include a tapered configuration, such as a taper from bottom to top or top to bottom.

Figure 2:
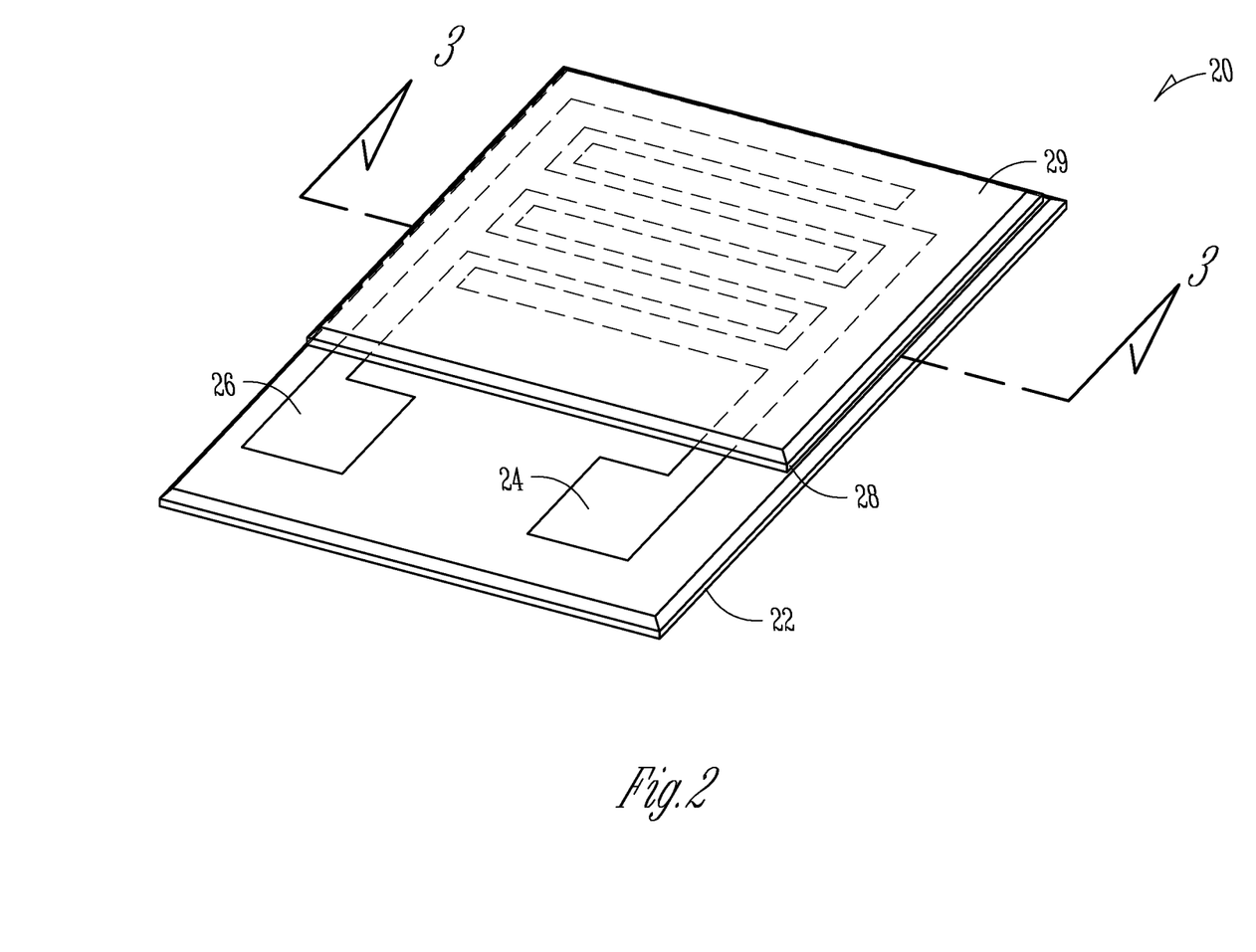
FIG. 2 shows a partial cut-away perspective view of a relative humidity sensor, in accordance with at least one example.

FIG. 2 shows a partial cut-away perspective view of a relative humidity sensor 20 (hereinafter also referred to as "sensor 20"), in accordance with at least one example. The sensor 20 is similar to sensor 10 as described in relation to FIG. 1, but illustrates an interdigitated configuration. For example, the sensor 20 can include a dielectric substrate 22, similar to the dielectric substrate 2 described in relation to FIG. 1.

As shown in the example of FIG. 2, the sensor 20 can include interdigitated electrodes (IDEs), including the first electrode 24 and the second electrode 26, both of which are supported by the dielectric substrate 22. The IDEs 24, 26 can be supported by the dielectric substrate 22 such as be depositing the IDEs 24, 26 on a surface of the dielectric substrate, as described herein. The first and second electrodes 24, 26 can include two individually addressable interdigitated comb-like electrode structures. In an example, the first and second electrodes 24, 26 can be direct printed on the dielectric substrate 2. The first and second electrodes 24, 26 can include the same materials as the first and second electrodes 4, 6 described in relation to sensor 10 of FIG. 1.

As shown in FIG. 2, the sensor 20 can include a sensitive layer 28 configured to detect humidity of the environment in which the sensor 20 is located. That is, the sensitive layer 28 can be in electrical contact with the IDEs, such that dielectric properties of the sensor 20 can vary based on the interaction between the sensitive layer 28 and the first and second electrodes 24, 26. The sensitive layer 28 can be formed of the composition of a polyimide and a hydrophobic filler, as discussed herein. Further, the sensor 20, as shown, can include a dust protection layer 29. As shown in FIG. 2, in an example, the dust protection layer 29 can cover at least a top surface of the sensitive layer 28. The dust protection layer 29 can be formed from the same materials as discussed in connection with the dust protection layer 12 of sensor 10 in FIG. 1.

Figure 3:
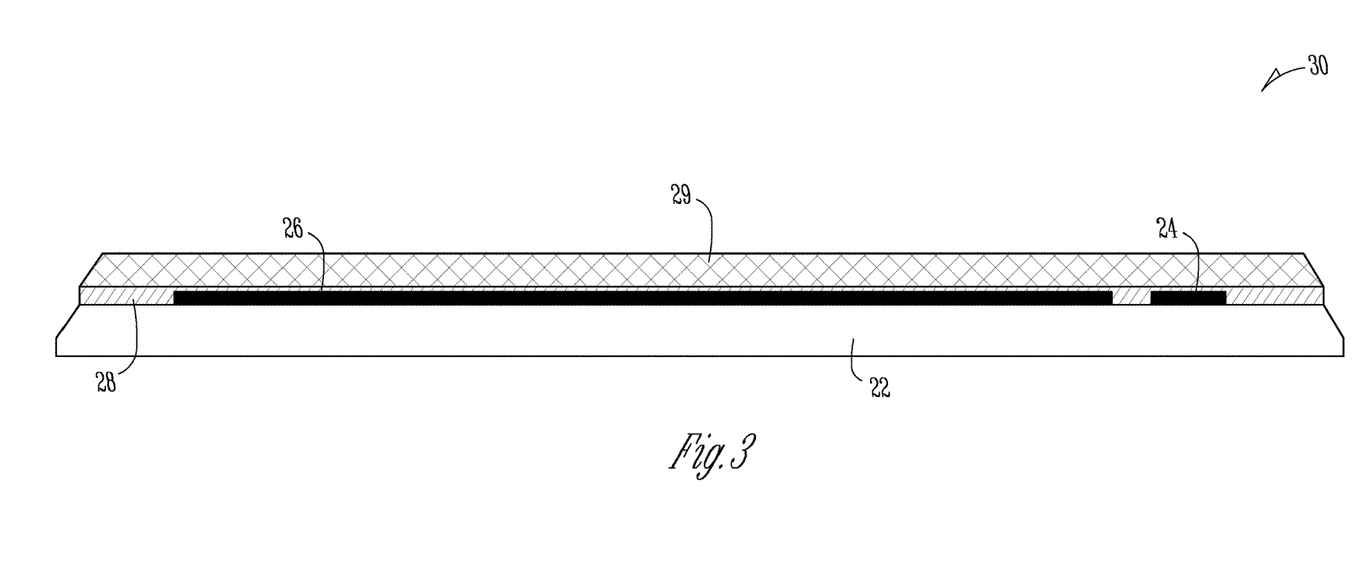
FIG. 3 shows a cross-sectional view of a relative humidity sensor, in accordance with at least one example.

FIG. 3 shows a cross-sectional view 30 of the sensor 20 in FIG. 2. The sensor can include the dielectric substrate 22. The dielectric substrate 22 can include the materials described above with respect to the dielectric substrate (e.g., 2, FIG. 1). The interdigitated electrodes, the first electrode 24 and the second electrode 26, can be deposited on the dielectric substrate 22, such as by a direct printing method. In an example, the sensitive layer 28 can be deposited on the IDEs so as to encompass the first and second electrodes 24, 26 and form a thin layer above the IDEs 14A, 14B. As shown in FIG. 3, the sensor can include the dust protection film 29 above the sensitive layer 28, as described herein.

Figure 4:
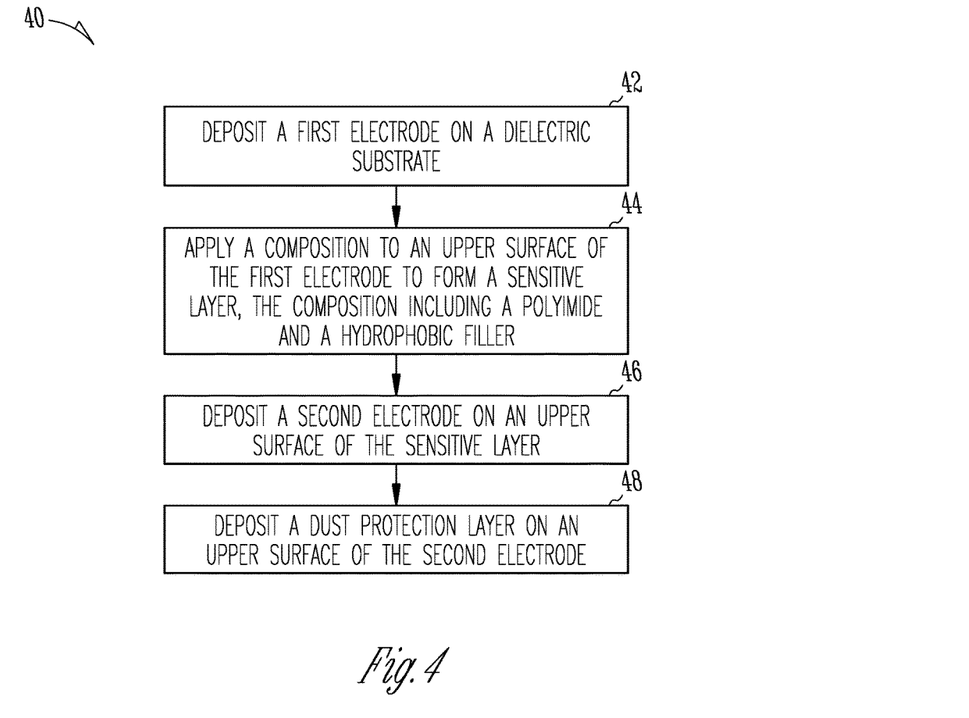
FIG. 4 shows a method of forming a relative humidity sensor, in accordance with at least one example.

FIG. 4 illustrates a method 40 of forming a relative humidity sensor, in accordance with at least one example. At 42, the method 40 can includes depositing a first electrode on a dielectric substrate, such as the dielectric substrate 2 of FIG. 1. The first electrode can include an electrode as described herein, such as the first electrode 4 of FIG. 1. In an example, depositing the first electrode can include direct printing. The method 40 can include applying a composition to an upper surface of the first electrode to form a sensitive layer, at 44. The composition can include a polyimide and a hydrophobic filler, as described herein. In an example, the composition can be prepared by dissolving the hydrophobic filler in dimethylformamide (DMF), N-methylformamide (NMF), or both. In such an example, the hydrophobic filler can include an organic compound, such as a lignin, as described herein.

In an example, the method 40 can include preparing the composition by functionalizing a polyimide, such as a commercially available polyimide described herein. The functionalization can include using the chemical reduction of aryl diazonium salt of 4 amino-biphenyl, p-toluidine, p-ethyl aniline, p-isopropyl aniline, and p-tertbutylaniline. From the chemical reduction, aryl diazonium salts are generated in-situ in the presence of HCl 0.2M and $NaNO_2$. After this, $H_3PO_2$ is added to the solution in order to reduce the aryl diazonium salt. The corresponding aryl radicals react with the polyimides, which are dipped in the solution. The polyimides can be dissolved either in DMF, NMP, or both. In such an example, the hydrophobic filler can include talc nanoparticles, as described herein. A solution of talc nanoparticles and DMF can be stirred and then mixed with the functionalized polyimide solution to form the composition. As an example, the functionalization of the polyimide P84® is shown below. Chemical equation (5) show the generation of an aryl radical from the reduction of a diazonium compound and the displacement of the $N_2$ group (e.g., arenediazonium cations reduced by hypophosphorous acid $H_2PO_2$). Chemical formulas (6) illustrate examples of R-groups for the diazonium compound in chemical equation (5). Chemical formulas (7)-(9) show the further products of the corresponding aryl radicals reacting with the polyimides.

(5)

where R could be:

(6)

(7)

At 46, the method 40 can include depositing a second electrode on an upper surface of the sensitive layer, such as the second electrode 8 as described in relation to FIG. 1. In an example, the method 40 can include depositing a dust protection layer, such as the dust protection layer 12 of FIG. 1, on an upper surface of the second electrode, so as to form the relative humidity sensor.

Figure 5:
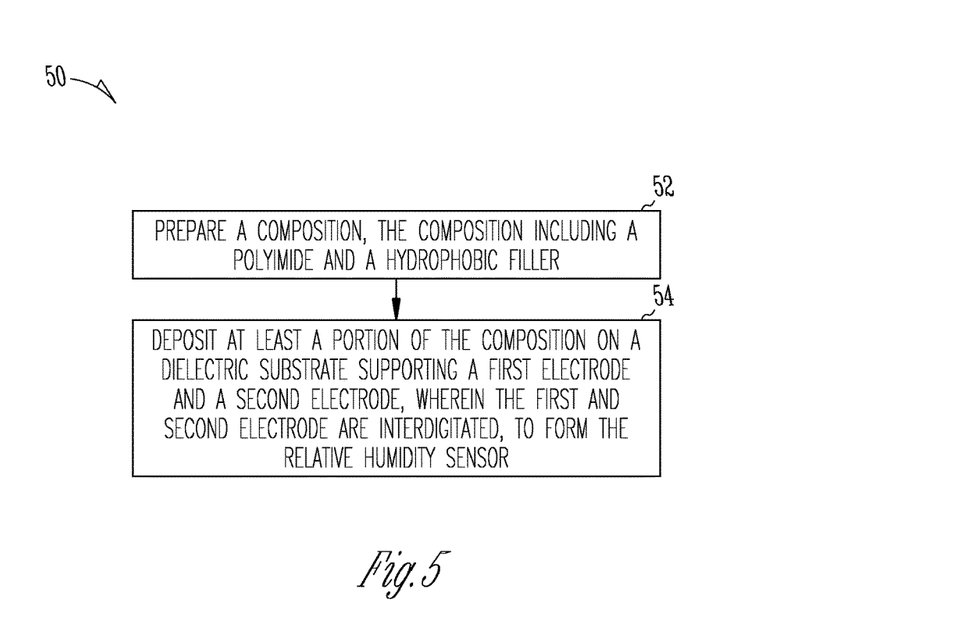
FIG. 5 shows a method of forming a relative humidity sensor, in accordance with at least one example.

FIG. 5 illustrates a method 50 of forming a humidity sensor, in accordance with at least one example. At 52, the method includes preparing a composition including a polyimide and a hydrophobic filler. The composition prepared at 52 can be prepared by any method described herein, such as in relation to FIGS. 1-4. At 54, the method 50 can include depositing at least a portion of the composition on a dielectric substrate supporting a first electrode and a second electrode, wherein the first and the second electrode are interdigitated (24, 26 of FIG. 2), to form the relative humidity sensor (20 of FIG. 3). In an example, the method 50 can include depositing a dust protection layer on at least an upper surface of the second electrode, as described herein.

EXAMPLES

Examples of the present disclosure provide a relative humidity sensor configured to detect the presence of relative humidity by an increase in capacitance of a sensitive layer placed between two metal electrodes.

Example 1 includes subject matter directed toward a relative humidity sensor, comprising a first electrode and a second electrode disposed above a dielectric substrate; a sensitive layer disposed above at least one of the first electrode and the second electrode, the sensitive layer is formed from a composition including a polyimide and a hydrophobic filler; and a dust protection layer disposed above the sensitive layer.

In Example 2, the subject matter of Example 1 can be optionally configured wherein the hydrophobic filler is organic.

In Example 3, the subject matter of Examples 1 or 2 can be optionally configured wherein the hydrophobic filler is one or more lignin.

In Example 4, the subject matter of Examples 1-3 can be optionally configured wherein the one or more lignin is about 1 to about 10 weight percent based on a total weight of the composition.

In Example 5, the subject matter of Examples 1-4 can be optionally configured wherein the one or more lignin has an average molecular weight between about 500 and about 1000 grams/mol.

In Example 6, the subject matter of Examples 1-5 can be optionally configured wherein the hydrophobic filler is inorganic.

In Example 7, the subject matter of Examples 1-6 can be optionally configured wherein the hydrophobic filler is talc nanoparticles.

In Example 8, the subject matter of Examples 1-7 can be optionally configured wherein the talc nanoparticles is hydrated magnesium covered silica having the chemical formula $Mg_3Si_4O_{10}(OH)_2$.

In Example 9, the subject matter of Examples 1-8 can be optionally configured wherein the talc nanoparticles are about 1 to about 5 weight percent based on a total weight of the composition.

In Example 10, the subject matter of Examples 1-9 can be optionally configured wherein the sensitive layer is disposed above the first electrode and the second electrode is disposed above the sensitive layer.

In Example 11, the subject matter of Examples 1-10 can be optionally configured the first electrode and the second electrode are interdigitated and the sensitive layer is disposed above the first electrode and the second electrode.

In Example 12, the subject matter of Examples 1-11 can be optionally configured wherein dust protection layer is more porous and thus less hydrophobic than the sensitive layer.

In Example 13, includes subject matter directed toward a method of forming a relative humidity sensor, the method comprising depositing a first electrode on a dielectric substrate; applying a composition to an upper surface of the first electrode to form a sensitive layer, the composition including a polyimide and a hydrophobic filler; depositing a second electrode on an upper surface of the sensitive layer; and depositing a dust protection layer on an upper surface of the second electrode.

In Example 14, includes subject matter directed towards a method of forming a relative humidity sensor, the method comprising: preparing a composition, the composition including a polyimide and a hydrophobic filler; and depositing at least a portion of the composition on a dielectric substrate supporting a first electrode and a second electrode, wherein the first and second electrode are interdigitated, to form the relative humidity sensor.

In Example 15, the subject matter of Examples 1-14 can be optionally configured to further comprise functionalizing the polyimide using a chemical reduction of aryl diazonium salts; preparing a solution including the hydrophobic filler and dimethylformamide (DMF), wherein the hydrophobic filler include talc nanoparticles; and stirring the solution with the functionalized polyimide to form the composition.

The above Detailed Description is intended to be illustrative, and not restrictive. For example, the above-described examples or one or more elements thereof may be used in combination with each other. Other embodiments may be used, such as by one of ordinary skill in the art upon reviewing the above description. In addition, various features or elements may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the phrase "varus/valgus angle" is used to refer to a varus angle only, a valgus angle only, or both a varus angle and a valgus angle.

In the appended claims, the terms "including" and "in which" are used as the plain-English equivalents of the respective terms "comprising" and "wherein." The terms "including" and "comprising" are open-ended, that is, a system or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

All publications, including non-patent literature (e.g., scientific journal articles), patent application publications, and patents mentioned in this specification are incorporated by reference as if each were specifically and individually indicated to be incorporated by reference.

The Abstract is provided to allow the reader to ascertain the nature of the technical disclosure quickly. It is submitted with the understanding that it will not be used to interpret or limit the scope or meaning of the claims.

What is claimed is:

1. A relative humidity sensor, comprising:
   a first electrode and a second electrode disposed above a dielectric substrate;
   a sensitive layer disposed above at least one of the first electrode and the second electrode, the sensitive layer is formed from a composition including a polyimide and a hydrophobic filler dispersed among the polyimide; and
   a dust protection layer disposed above the sensitive layer.

2. The relative humidity sensor of claim 1, wherein the hydrophobic filler is organic.

3. The relative humidity sensor of claim 2, wherein the hydrophobic filler is one or more lignin.

4. The relative humidity sensor of claim 3, wherein the one or more lignin is about 1 to about 10 weight percent based on a total weight of the composition.

5. The relative humidity sensor of claim 3, wherein the one or more lignin has an average molecular weight between about 500 and about 1000 grams/mol.

6. The relative humidity sensor of claim 1, wherein the hydrophobic filler is inorganic.

7. The relative humidity sensor of claim 6, wherein the hydrophobic filler is talc nanoparticles.

8. The relative humidity sensor of claim 7, wherein the talc nanoparticles is hydrated magnesium covered silica having the chemical formula $Mg_3Si_4O_{10}(OH)_2$.

9. The relative humidity sensor of claim 7, wherein the talc nanoparticles are about 1 to about 5 weight percent based on a total weight of the composition.

10. The relative humidity sensor of claim 1, wherein the sensitive layer is disposed above the first electrode and the second electrode is disposed above the sensitive layer.

11. The relative humidity sensor of claim 1, wherein the first electrode and the second electrode are interdigitated and the sensitive layer is disposed above the first electrode and the second electrode.

12. The relative humidity sensor of claim 1, wherein dust protection layer is more porous and less hydrophobic than the sensitive layer.

13. A method of forming a relative humidity sensor, the method comprising:
    depositing a first electrode on a dielectric substrate;
    applying a composition to an upper surface of the first electrode to form a sensitive layer, the composition including a polyimide and a hydrophobic filler dispersed among the polyimide;

depositing a second electrode on an upper surface of the sensitive layer; and depositing a dust protection layer on an upper surface of the second electrode.

14. The method of claim 13, wherein the hydrophobic filler is one of: one or more lignin and talc nanoparticles.

15. The method of claim 14, wherein the hydrophobic filler is one or more lignin and the one or more lignin has an average molecular weight between about 500 and about 1000 grams/mol.

16. The method of claim 14, wherein the hydrophobic filler is the talc nanoparticles and the talc nanoparticles are about 1 to about 5 weight percent based on a total weight of the composition.

17. The method of claim 16, wherein the talc nanoparticles is hydrated magnesium covered silica having the chemical formula $Mg_3Si_4O_{10}(OH)_2$.

18. The method of claim 13, wherein dust protection layer is more porous and less hydrophobic than the sensitive layer.

19. A method of forming a relative humidity sensor, the method comprising:

preparing a composition, the composition including a polyimide and a hydrophobic filler dispersed among the polyimide; and depositing at least a portion of the composition on a dielectric substrate supporting a first electrode and a second electrode, wherein the first and second electrode are interdigitated, to form the relative humidity sensor.

20. The method of claim 19, wherein preparing the composition includes:

functionalizing the polyimide using a chemical reduction of aryl diazonium salts;

preparing a solution including the hydrophobic filler and dimethylformamide (DMF), wherein the hydrophobic filler include talc nanoparticles; and stirring the solution with the functionalized polyimide to form the composition.

* * * * *